United States Patent
Finarov et al.

(10) Patent No.: US 7,313,425 B2
(45) Date of Patent: Dec. 25, 2007

(54) DEVICE AND METHOD FOR NON-INVASIVE OPTICAL MEASUREMENTS

(75) Inventors: Alexander Finarov, Rehovot (IL); Ilya Fine, Rehovot (IL)

(73) Assignee: Orsense Ltd., Rehovot (IL)

( * ) Notice: Subject to any disclaimer, the term of this patent is extended or adjusted under 35 U.S.C. 154(b) by 271 days.

(21) Appl. No.: 10/885,885

(22) Filed: Jul. 8, 2004

(65) Prior Publication Data

US 2006/0009685 A1    Jan. 12, 2006

(51) Int. Cl.
*A61B 5/00*    (2006.01)

(52) U.S. Cl. ........................ 600/310; 600/344

(58) Field of Classification Search .............. 600/310, 600/316, 322, 323, 335, 344
See application file for complete search history.

(56) References Cited

U.S. PATENT DOCUMENTS

| | | | |
|---|---|---|---|
| 4,685,464 A | | 8/1987 | Goldberger et al. |
| 4,825,872 A | * | 5/1989 | Tan et al. ................... 600/344 |
| 5,057,695 A | | 10/1991 | Hirao et al. |
| 5,069,214 A | | 12/1991 | Samaras et al. |
| 5,152,296 A | | 10/1992 | Simons |
| 5,425,360 A | * | 6/1995 | Nelson ........................ 600/323 |
| 5,782,757 A | | 7/1998 | Diab et al. |
| 5,817,010 A | * | 10/1998 | Hibl ............................ 600/344 |
| 5,974,337 A | * | 10/1999 | Kaffka et al. ............... 600/322 |
| 6,018,673 A | * | 1/2000 | Chin et al. .................. 600/322 |
| 6,115,621 A | | 9/2000 | Chin |
| 6,213,952 B1 | | 4/2001 | Finarov et al. |
| 6,222,189 B1 | | 4/2001 | Misner et al. |
| 6,285,894 B1 | | 9/2001 | Oppelt et al. |
| 6,400,972 B1 | | 6/2002 | Fine |
| 6,461,305 B1 | | 10/2002 | Schnall |
| 6,537,225 B1 | * | 3/2003 | Mills .......................... 600/481 |
| 6,801,798 B2 | | 10/2004 | Geddes et al. |
| 2002/0077535 A1 | | 6/2002 | Finarov et al. |
| 2002/0173709 A1 | | 11/2002 | Fine et al. |
| 2003/0036690 A1 | | 2/2003 | Geddes et al. |
| 2004/0054290 A1 | | 3/2004 | Chance |

FOREIGN PATENT DOCUMENTS

| | | |
|---|---|---|
| WO | WO 99/65384 | 12/1999 |
| WO | WO 01/26539 A1 | 4/2001 |
| WO | WO 01/45553 A1 | 6/2001 |
| WO | WO 01/67946 A1 | 9/2001 |
| WO | WO 01/96872 A2 | 12/2001 |
| WO | WO 2004/105596 A1 | 12/2004 |
| WO | WO 2004/112574 A2 | 12/2004 |

\* cited by examiner

*Primary Examiner*—Eric F Winakur
(74) *Attorney, Agent, or Firm*—Browdy and Neimark, PLLC

(57) ABSTRACT

An optical measurement device and method are presented for use in non-invasive measurements on a patient's body. The device comprises an illumination assembly configured and operable to generate illuminating light of a predetermined wavelength range; a detection assembly; and a light directing assembly. The detection assembly comprises a first detector unit for detecting a first light signal transmitted through an illuminated body portion and generating first measured data indicative of the detected transmitted light, and a second detector unit for detecting a second light signal reflected from the illuminated body portion and generating second measured data indicative of the detected reflected light. The light directing assembly comprises a light diffuser for scattering back light incident thereto, to thereby direct the illuminating light or the light coming from the body portion back towards the body portion. This technique provides for increasing the amount of light reaching a region of interest inside the body portion and maximizing homogeneity of the first and second detected light signals.

46 Claims, 4 Drawing Sheets

DEVICE AND METHOD FOR NON-INVASIVE OPTICAL MEASUREMENTS

FIELD OF THE INVENTION

This invention relates to a device and method for non-invasive optical measurements on a human body, which is particularly useful for measuring blood-related parameters.

BACKGROUND OF THE INVENTION

Non-invasive (in vivo) methods for measuring various blood-related parameters have become very popular due to the fact that these measurements, in distinction to invasive ones, do not involve the physical withdrawal of a blood sample from the patient's body. Optical monitoring techniques of the kind specified utilize the detection of light transmitted or reflected from the location on the patient's body under measurement, and are based on spectrophotometric measurements enabling the indication of the presence of various blood constituents based on known spectral behaviors of these constituents. These methods being applied in real medicine rather than in analytical chemistry create the basis for non-invasive blood tests, which present, no doubt, one of today's most exciting challenges. To make blood tests low-cost, safe and painless means to make them non-invasive.

The two main challenges, that any non-invasive optical method has to deal with, are as follows: (1) the low signal-to-noise ratio, and, (2) the large variability of individual parameters influencing the signal of concrete patients.

Most of these techniques utilize a measurement optical device or probe, designed in a manner to be attached to the patient's finger, which includes an optical assembly for irradiating the finger with light and detecting its light response. The conventional devices of the kind specified, such as a pulse oximeter, which is the generally accepted standard of everyday clinical practice, provide for measuring enhanced optical pulsatile signals caused by the changes in the volume of a blood flowing through a fleshy medium (e.g., finger).

It is known that for blood parameters other than oxygen saturation, e.g., glucose concentration, significant difficulties have been encountered, because their absorption spectral behavior in red and near infrared regions is not as remarkable as for the oxygenized hemoglobin. Hence, the main limitations on the way of expanding the non-invasive techniques to the measurements different from pulse oximetry are associated with the limited selectivity of the absorption based method.

A different technique is disclosed in U.S. Pat. No. 6,400,972, WO 01/45553 and WO 01/96872, all assigned to the assignee of the present application. This is an occlusion-release based technique, according to which an over-systolic pressure is applied to the blood perfused fleshy medium with a normal blood flow so as to create a state of temporary blood flow cessation at the measurement location. The measurement with different wavelengths of incident radiation and/or different polarization states of detected light are carried out at timely separated sessions taken during a time period including a cessation time when the state of the blood flow cessation is maintained. This technique utilizes the condition of the "artificial blood kinetics" rather than the natural blood kinetics taking place when the state of blood cessation is not achieved. As a result of the cessation of the blood flow, a condition of the artificial kinetics is achieved with the optical characteristics of the blood associated with the light response being different from those at the natural blood kinetics. Indeed, it is known that the scattering properties of blood depend on the size and shape of scatterers (aggregates). Thus, time changes of the light response at the condition of artificial kinetics depend on the changes in the shape and average size of the scattering centers in the medium, i.e., red blood cells (RBC) aggregation (Rouleaux effect). It was found that owing to the effect of the artificial kinetics, the optical characteristics of blood changes dramatically, such that they differ from those of the fleshy medium with a normal blood flow by about 25 to 60%, and sometimes even more. Hence, the accuracy (i.e., signal-to-noise ratio) of the technique based on the artificial kinetics as well as selectivity of the optical measurements can be substantially better when compared with those based on measurements of the blood parameters at natural kinetics.

SUMMARY OF THE INVENTION

There is a need in the art to facilitate non-invasive optical measurements of blood parameters by providing a novel device and method capable of stabilizing the optical response of an illuminated region in a patient's body.

The present invention provides for detecting the optical response formed by both light reflected from the illuminated body portion and light transmitted therethrough. It should be understood that the terms "reflected light" and "transmitted light" used herein signify light components detected at, respectively, the same side of the body portion at which the illumination is applied and the opposite side, and actually both light portions include light scattered from the illuminated region.

The present invention utilizes redirecting reflections of light on its way towards the region of interest (i.e., blood vessel) back to the region of interest. This is implemented using a diffuser accommodated in the optical path of light reflected from the body portion under measurements. Due to the provision of a diffuser, illuminating light that is reflected from the skin and bones is "collected" and directed back to the region of interest. The use of a diffuser stabilizes both the reflected and transmitted responses of the illuminated region, and causes a stable increase of the reflected signal.

Thus, according to one aspect of the invention, there is provided an optical measurement device for use in non-invasive measurements on a patient's body, the device comprising:

an illumination assembly configured and operable to generate illuminating light of a predetermined wavelength range;

a detection assembly comprising a first detector unit for detecting a first light signal transmitted through an illuminated body portion and generating first measured data indicative of the detected transmitted light, and a second detector unit for detecting a second light signal reflected from the illuminated body portion and generating second measured data indicative of the detected reflected light; and a light directing assembly comprising a light diffuser for scattering back light incident thereto, to thereby direct the illuminating light or the light coming from the body portion back towards the body portion, thereby increasing amount of light reaching a region of interest inside the body portion and thus maximizing homogeneity of the first and second detected light signals.

Preferably, the light diffuser extends along at least a part of the body portion at the illuminated side thereof. The diffuser may be formed with an optical window for allowing passage of light from the illumination assembly towards the body portion; and/or with an optical window for allowing light passage from the body portion to the second detector unit.

The diffuser may for example be, but not limited to, of dimensions of about 20×24 mm, and may be made of a material such as PVC, Polyurethan.

The device may be configured for operating in the occlusion-release mode. To this end, the device includes a pressurizing assembly operable for applying an over-systolic pressure to the patient's body so as to create a condition of artificial blood kinetics in the region of interest and maintain this condition for a certain time period. The pressurizing assembly may be configured and operable for applying a secondary controllably varying under- or over-systolic pressure to the body within the region of interest, so as to alter said condition of artificial blood kinetics over a predetermined time interval within said certain time period, to thereby modulate the amount of blood under measurements.

Preferably, the device is configured as finger holder. This may be a clip member for enclosing the body portion between its upper and lower arms, one of the upper and lower arms carrying the illumination assembly, the diffuser and the second detector unit, and the other arm carrying the first detector unit. Alternatively, this may be a ring-like device. For example, such a ring may be designed as two U-shaped semi-ring portions, one carrying the illumination assembly, the diffuser and the second detector unit, and the other carrying the first detector unit. If the occlusion-mode operation is considered, the pressurizing assembly is associated with one of the U-shaped portions being in the form of an air cushion on the inner side of said portion, in which case the air cushion is made of a light diffusing material, thereby presenting said diffuser.

According to another aspect of the invention, there is provided a method for use in non-invasive optical measurements on a patient's body utilizing illumination of a region of interest inside the body portion and detection of light response of the region of interest, the method comprising:

collecting light coming from the body portion and directing at least a part of the collected light back to the body portion;

detecting a first light signal transmitted through the body portion and generating first measured data indicative of the detected transmitted light, and detecting a second light signal reflected from the body portion and generating second measured data indicative of the detected reflected light; the method providing for increasing amount of light reaching the region of interest inside the body portion, and for maximizing homogeneity of the first and second detected light signals.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
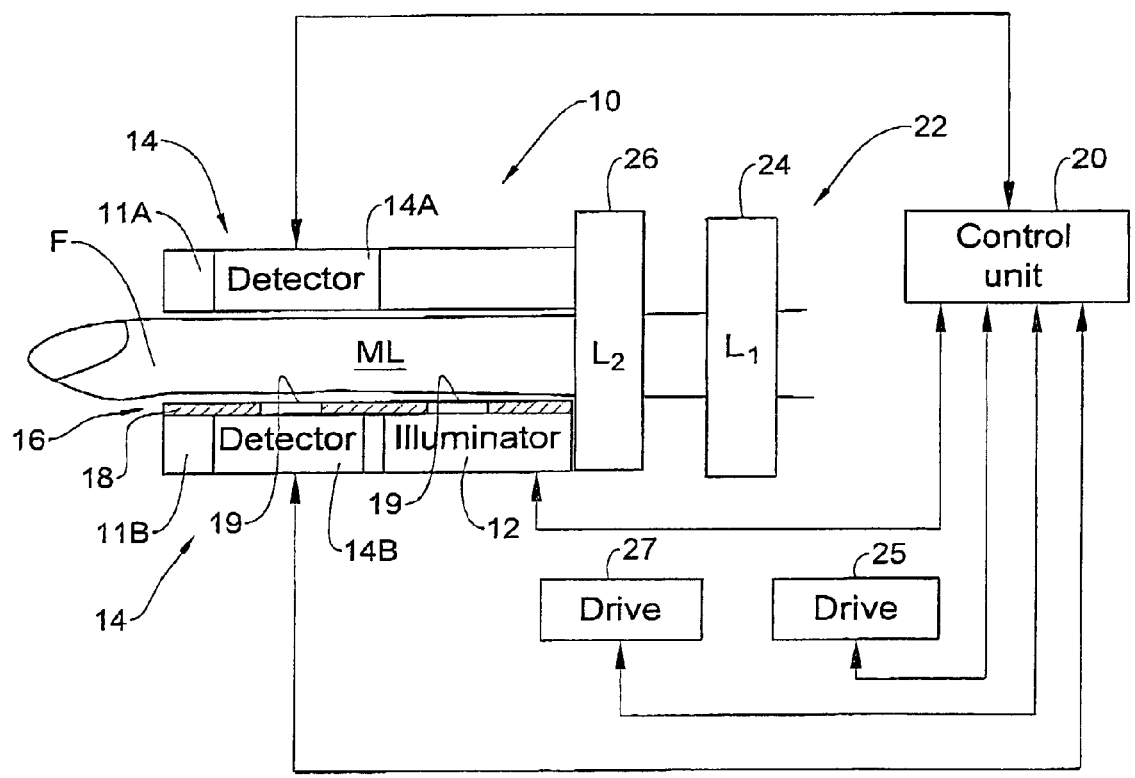
FIG. 1 is a schematic illustration of a measurement device of the present invention utilizing a diffuser.

Referring to FIG. 1, there is schematically illustrated an optical measurement device 10 of the present invention for use in non-invasive measurements on a patient's body, e.g., patient's finger F. The device 10 includes an illumination assembly 12; a detection assembly 14; and a light directing assembly 16. A control unit 20 is provided for operating the illumination and detection assemblies and for receiving and processing measured data coming from the detection assembly.

The illumination assembly 12 is accommodated so as to direct illuminating light towards the finger F. The illumination assembly 12 may utilize one or more light emitting elements, e.g., LED(s). Preferably, a matrix of LEDs is used. In this specific example of measuring blood parameters, the illumination assembly 12 is designed for generating light of different wavelengths (at least two different wavelengths), which can be implemented by using different light emitting elements or a single broadband illuminator.

The light detection assembly 14 includes a first detector unit 14A accommodated substantially opposite the illumination assembly 12 for detecting a first light signal transmitted through the finger F and generating first measured data $MD_1$ indicative thereof, and includes a second detector unit 14B accommodated adjacent to the illumination assembly 12 for detecting a second light signal reflected from the inside of the finger and generating second measured data $MD_2$ indicative thereof. Each of the detector units 14A and 14B includes one or more frequency selective detector (e.g., a matrix of detectors), such as spectrophotometer and/or photodiode typically equipped with frequency selective filter and amplifying means, which are not specifically shown.

It should be understood that generally, the light emitting element(s) as well as a detectors may be accommodated aside the finger in which case light is directed towards and away from the respective locations on the finger via fibers.

The light directing assembly 16 includes a diffuser 18 accommodated proximate the finger portion under measurements at the illuminating side, so as to collect light reflections from the finger and reflect them back towards the inside of the finger, thereby increasing the amount of light reaching the blood vessel in the finger. As shown in the present example, the diffuser 18 extends along the finger portion and is formed with an optical window 19 so as to allow passage of illuminating light towards the finger. The reflection-mode detector unit 14B may be accommodated adjacent to the diffuser slightly aside thereof to detect reflected light propagating along axes that do not intersect with the diffuser, or alternatively, may be vertically aligned with the diffuser in which case the diffuser 18 is formed with an additional optical window 19 allowing passage of light therethrough towards the detector 14B.

The diffuser is made of a semi-transparent material, capable to diffuse visible and near-infrared light. The attenuation coefficient and spatial distribution of diffused light has to be a very weak function of wavelength in the operating spectral region. The diffuser has a certain minimal size so as to ensure that the majority of the body surface (e.g., surface of the patient's finger provides efficient return of reflected light to the examined media (e.g., about 48 $mm^2$, e.g., dimensions of about 20×24 mm).

The diffuser thus "collects" light that is typically reflected from the skin and bone while propagating towards the blood vessel and reflects this light back to the blood vessel to thereby increase the amount of light reaching the blood vessel. As a result, both the intensity of light transmitted through the blood vessel and received at the first detector unit 14A (transmission-mode detector) and the intensity of light reflected from the blood vessel and received at the second detector unit 14B (reflection-mode detector) are increased, and the homogeneity of the first and second light signals is thus maximized.

The device 10 may be designed as a finger holder in the form of a clip member attachable to a patient's finger so as to enclose a finger portion between upper and lower arms 11A and 11B of the clip member (similar to the conventionally used pulse oximeter). One of the upper and lower arms—lower arm 11B in the present example, carries the illumination assembly 12, the diffuser 18 and the reflection-mode detector unit 14B, and the other arm 11A carries the transmission-mode detector unit 14A. The diffuser 18 extends along at least a part of the inner surface of the lower arm 11B of the clip member.

Preferably, the measurement device 10 is configured for operating with the so-called "occlusion-release mode". To this end, the device 10 includes a pressurizing assembly 22 having an occluder arrangement (occlusion cuff) 24 associated with a drive mechanism 25 operable by the control unit 20 for applying an over-systolic pressure to the patient's finger F to create a state of blood flow cessation in the vicinity of a measurement location ML (where optical measurements are applied). The pressurizing assembly 22 may also be operable to apply a secondary controllably varying under- or over-systolic pressure to the measurement location ML, which in the present example of FIG. 1 is implemented using another cuff 26 associated with a drive mechanism 27. Thus, the primary over-systolic pressure is applied to a finger location $L_1$ upstream of the measurement location ML with respect to the blood flow direction, and the variable secondary pressure is periodically applied to a location $L_2$ in the closest vicinity of the measurement location while in the state of temporarily blood flow cessation, thus implementing the so-called "multiple-occlusion" mode.

The principles of the occlusion-release based measurements are disclosed in the above-indicated U.S. Patents and the multiple-occlusion mode is described in a co-pending U.S. patent application Ser. No. 10/452,932, all assigned to the assignee of the present application, and do not form part of the present invention.

Moreover, the principles of the present invention consisting of using a diffuser and detecting both light transmitted through and reflected from the region of interest, can advantageously be used in measurements based on detecting a pulsatile signal of a light response of the medium (such as in the conventional pulse oximeter), and in the occlusion-based measurements where a non-pulsatile signal is detected. This will be described further below with reference to FIGS. 3A-3B and 4A-4B.

It should be noted that when using the simultaneous transmission- and reflection-mode measurements, the parameter of interest (e.g., glucose concentration in blood) may be calculated independently from transmission and reflection signals. When a difference between the two readings exceeds a certain predetermined value, the measurement results are defined as an outlier.

Figure 2:
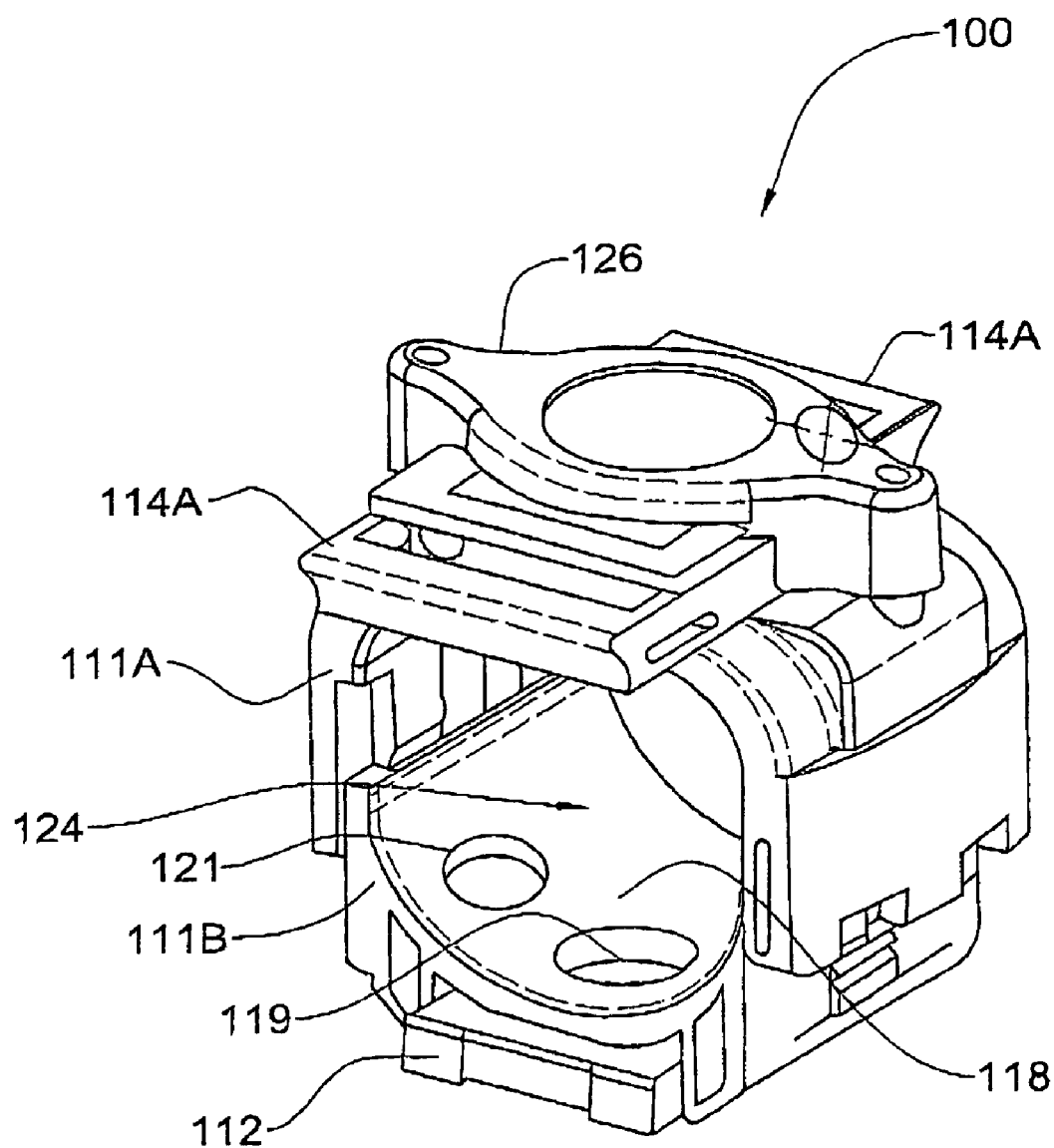
FIG. 2 illustrates a measurement device according to a specific example of the invention.

FIG. 2 illustrates a specific but not limiting example of a measurement device 100 of the present invention. In the present example, the device 100 is designed like a ring, formed by two portions 111A and 111B each of a substantially U-shaped cross-section arranged with respect to each other for enclosing and holding therebetween a portion of the patient's finger (not shown here). The U-shape parts 111A and 111B are made of a rigid or semi-rigid material, such as metal or plastic. In the cross-section, these U-shape parts can, for example, be of semi-circle or semi-oval forms. The parts 111A and 111B can partially overlap over a predetermined distance.

The measurement device (probe) 100 comprises an illumination assembly (not shown) mounted on a holding frame 112 associated with the semi-ring 111B; a light detection assembly including a transmission-mode detector unit (not shown) mounted on a holding frame 114A associated with the semi-ring 111A so as to be substantially opposite the illumination assembly, and a reflection-mode detector unit (not shown) mounted on the semi-ring 111B; and a diffuser 118 located on the inner surface of the semi-ring 111B. Similar to the previously described example, the illumination assembly can include a plurality of light sources (e.g., LEDs) associated with a suitable drive mechanism (not shown) operated by a control unit, or a single broad band illuminator. The light source (or multiple light sources) radiates the measurement location of the finger through an aperture (optical window) 119 in the diffuser 118. In the present example, another aperture 121 is provided in the diffuser 118 to allow passage of light from the illuminated region to the reflection-mode detector. It should, however, be understood that the provision of this aperture is optional since the reflection-mode deflector may be accommodated adjacent to the diffuser slightly aside thereof to detect reflected light propagating along axes that do not intersect with the diffuser.

It should also be noted that, although in the present examples of FIGS. 1 and 2, the diffuser is shown as constructional part of the illumination/detection arrangement of the measurement device (e.g., finger holder), the diffuser may be a separate element. For example, the diffuser may be configured to be put onto a finger, so as to be located between the finger and the illumination/detection arrangement of the measurement device. The diffuser may be in the form of a thin elastic cover for wrapping at least a part of the body portion (e.g., finger), and configured to enable optical measurements therethrough. For example, the diffuser may be formed with an optical window, which when the device is put in operation is aligned with the optical path of illuminating light, and possibly also including an additional optical window aligned with the reflection mode detector.

Turning back to FIG. 2, the device 100 further includes a pressurizing assembly that includes an air cushion 124 associated with a drive mechanism (not shown) and operable to apply pressure to the finger portion enclosed between the parts 111A and 111B. In the present example, the cushion 124 is made of a light diffusing material thus presenting the diffuser 118.

By moving the upper and lower parts 111A and 111B of the probe towards each other, a position of a finger therebetween is fixed. Then, a locking device 126 further fixes the parts 111A and 111B to thereby apply a certain preliminary pressure to start the measurement procedure. The locking device may be implemented by any suitable known means (e.g., including a teeth arrangement and a spring assembly) and is aimed at preventing the opening of the ring-like probe. Then, the cushion 124, which in the present example is associated with the lower semi-ring 111B, is operated to press the finger to the upper semi-ring 111A to thereby apply an over-systolic pressure (e.g., 220-250 mmHg) and create a blood flow cessation in the finger. Then, during the measurements while in the blood flow cessation state, a variable over-systolic secondary pressure is supplied through the cushion 124. Thus, according to this embodiment of the invention, the primary over-systolic pressure as well as the secondary pressure is applied to the same location on the finger via the same pressurizing assembly (cushion 124).

Due to the provision of the diffuser (18 in FIG. 1 and 118 in FIG. 2), light that while propagating from the illumination assembly towards the blood vessel in the finger is typically reflected from the skin and bone, is collected and reflected back to the blood vessel. As a result, both the intensity of light transmitted through the blood vessel and received by the transmission mode detector and the intensity of light reflected from the blood vessel and received by the reflection mode detector are increased. This maximizes the homogeneity of the detected light signals.

Figure 3A:
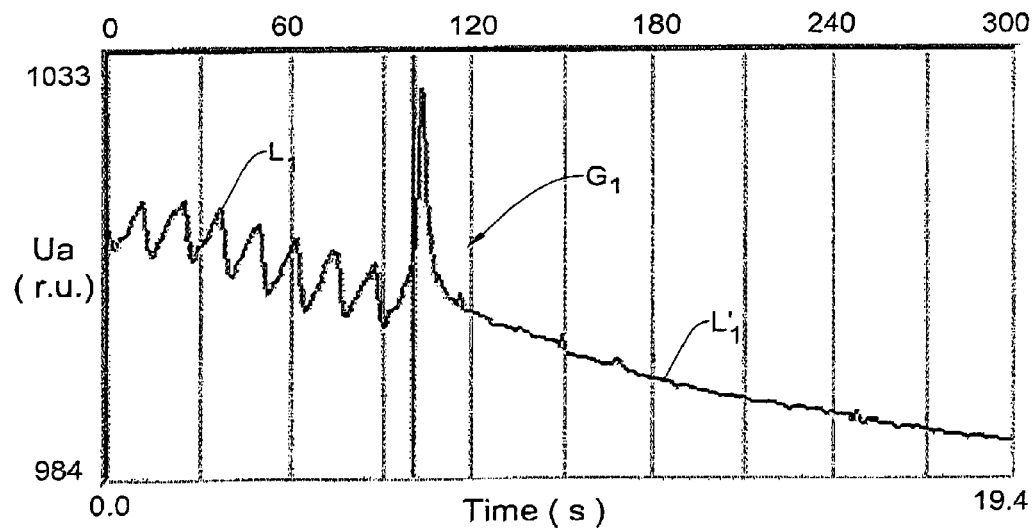
FIGS. 3A and 3B illustrate the result of typical optical measurements without a diffuser.
Figure 3B:
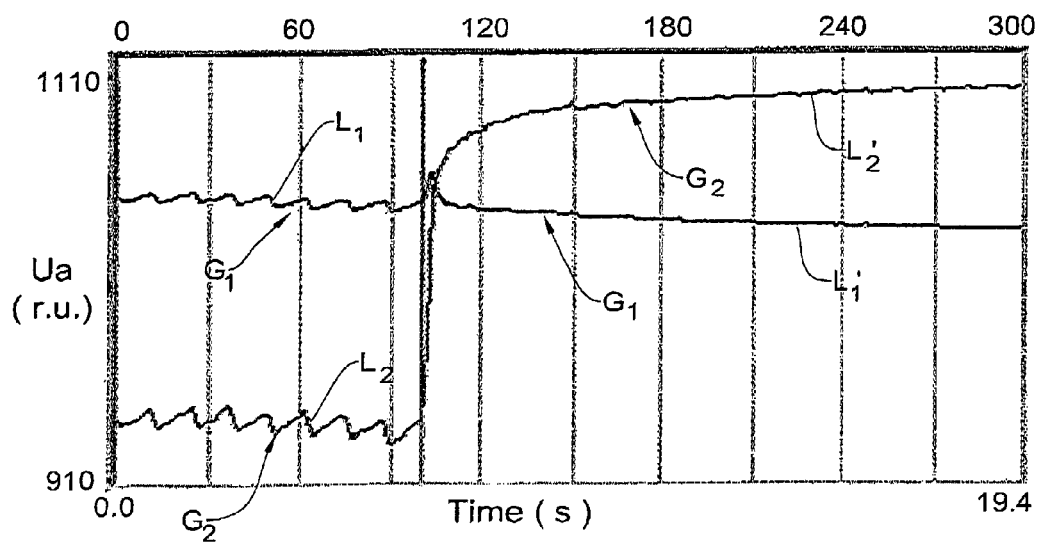
Figure 4A:
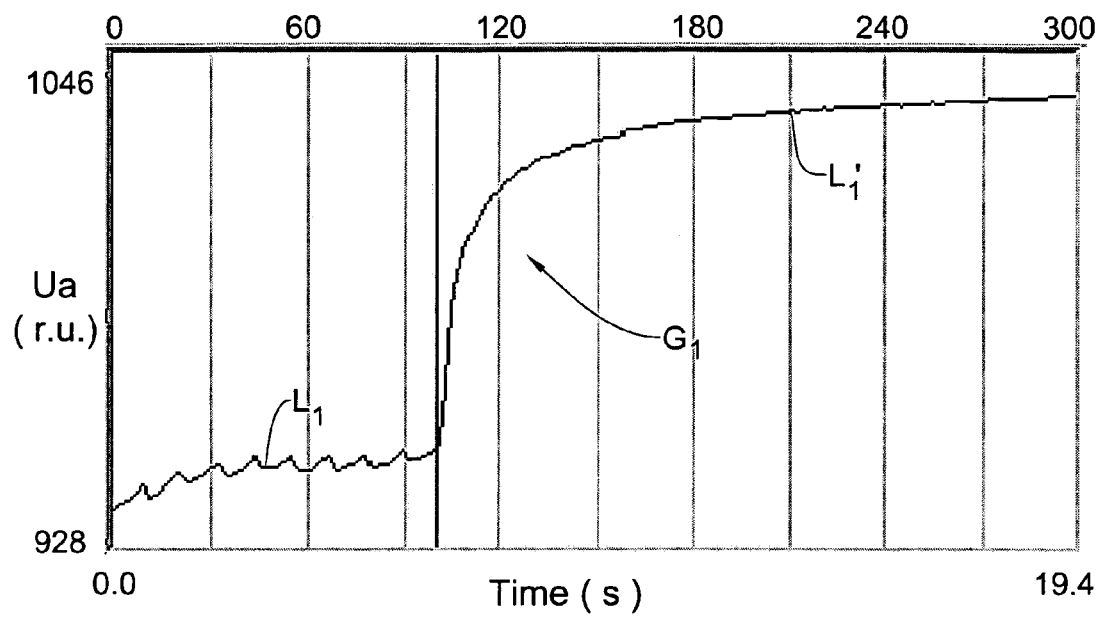
FIGS. 4A and 4B illustrate the results of measurements utilizing the device of the present invention with a diffuser.
Figure 4B:
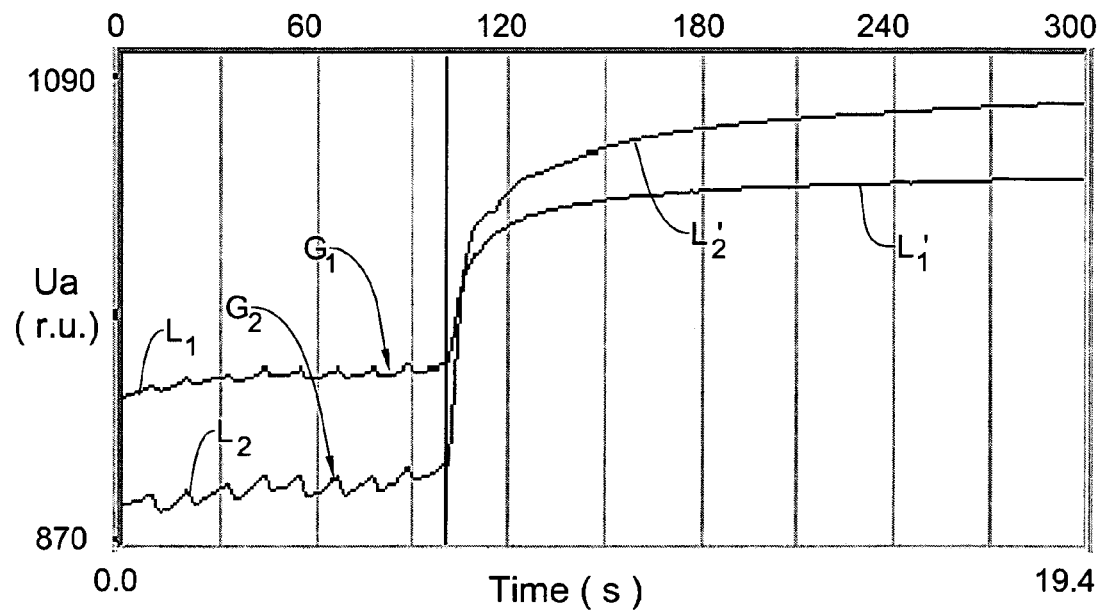

Reference is made to FIGS. 3A-3B and 4A-4B showing experimental results: FIGS. 3A and 3B illustrate the results of measurements with no diffuser and FIGS. 4A and 4B illustrate the same with the diffuser-based device of the present invention. Each of these figures shows the time variation of a detected light response of a measurement location inside a patient's finger.

In the example of FIG. 3A, the finger is illuminated with 720 nm light, and light reflected from the finger is measured. As shown, a graph $G_1$ has a pulsatile-signal part $L_1$ measured during a 100 sec time period prior to the application of an over-systolic pressure, and a non-pulsatile part $L'_1$ continuously measured after the application of such pressure. Both the pulsatile and non-pulsatile reflected signals decrease during the measurements. In the example of FIG. 3B, the finger is illuminated with 720 nm light, and time variations of light reflected from the finger $G_1$ and that of light transmitted through the finger $G_2$ are measured. Measured reflected signal $G_1$ has an initial pulsatile signal part $L_1$ and a further non-pulsatile signal part $L'_1$ resulting from the occlusion; and measured transmitted signal has initial pulsatile signal part $L_2$ and a further non-pulsatile signal part $L'_2$. As shown, the reflection occlusion-signal $L'_1$ decreases, and transmission occlusion-signal increases with time.

FIGS. 4A and 4B show the measurements with the diffuser for, respectively, reflection mode, and both reflection and transmission modes. As shown, when using the diffuser, all the signal parts increase during the measurements.

Those skilled in the art will readily appreciate that various modifications and changes can be applied to the embodiments of the invention as hereinbefore exemplified without departing from its scope defined in and by the appended claims.

The invention claimed is:

1. An optical measurement device for use in non-invasive measurements on a patient's body, the device comprising:
    an illumination assembly configured and operable to generate illuminating light of a predetermined wavelength range;
    a detection assembly configured and operable to concurrently provide transmission-mode and reflection-mode of light detection, the detection assembly comprising a first transmission-mode detector unit configured for detecting a first light signal indicative of the transmission of the illuminating light in the predetermined wavelength range through an illuminated body portion and generating first measured data indicative of the detected transmitted light, and a second reflection-mode detector unit operating simultaneously with said first detector and configured for detecting a second light signal indicative of the reflection of the illuminating light in the predetermined wavelength range from the illuminated body portion and generating second measured data indicative of the detected reflected light; and
    a light directing assembly comprising a light diffuser for scattering back light incident thereto, the light diffuser being oriented to redirect at least one of the illuminating, transmitted and reflected light components back towards the illuminated body portion to thereby cause further interaction of the redirected light with the body portion, and allow detection of the transmitted and reflected light components by said first and second detection units, thereby increasing amount of light reaching a region of interest inside the body portion and thus maximizing homogeneity of the first and second detected light signals.

2. The device of claim 1, wherein the light diffuser is located adjacent to the illumination assembly and, such that when the device is applied to the patient's body, the light diffuser extends along at least a part of the body portion at the illuminating side thereof.

3. The device of claim 2, wherein the diffuser is formed with an optical window for allowing passage of light from the illumination assembly towards the body portion.

4. The device of claim 3, wherein the diffuser has an additional optical window for allowing light passage from the body portion to the second detector unit.

5. The device of claim 1, wherein the light diffuser has at least one optical window for allowing light passage therethrough.

6. The device of claim 1, wherein the diffuser is made of a semi-transparent material, capable of diffusing visible and near-infrared light spectra.

7. The device of claim 1, wherein the diffuser is configured such that an attenuation coefficient and spatial distribution of diffused light is a very weak function of wavelength in said predetermined spectral rage.

8. The device of claim 1, wherein a minimal size for the diffuser is such as to ensure that majority of the body surface provides efficient return of reflected light to the region of interest in the body.

9. The device of claim 1, wherein the diffuser has a minimal size of about 48 mm$^2$.

10. The device of claim 1, wherein the detector unit includes a matrix of light detectors.

11. The device of claim 1, wherein the diffuser is mounted on a support arrangement supporting at least one of the illumination and detection assemblies.

12. The device of claim 1, wherein the diffuser is an elastic cover configured to wrap at least a part of the body portion under measurements.

13. The device of claim 12, wherein the diffuser has at least one optical window for allowing light passage therethrough.

14. The device of claim 1, wherein the diffuser is a disposable elastic cover configured to wrap at least a part of the body portion under measurements.

15. The device of claim 1, comprising a pressurizing assembly operable for applying an over-systolic pressure to the patient's body so as to create a condition of artificial blood kinetics in the region of interest and maintain this condition for a certain time period.

16. The device of claim 15, wherein said pressurizing assembly is operable to apply a secondary controllably varying pressure to the body within the region of interest, so as to alter said condition of artificial blood kinetics over a predetermined time interval within said certain time period, thereby to modulate scattering properties of blood.

17. The device of claim 1, wherein the illumination assembly comprises at least one light emitting element.

18. The device of claim 1, wherein the illumination assembly comprises a matrix of light emitting elements generating light of different wavelengths.

19. The device of claim 1, configured as a clip member for enclosing the body portion between its upper and lower arms, one of the upper and lower arms carrying the illumination assembly, the diffuser and the second detector unit, and the other arm carrying the first detector unit.

20. The device of claim 19, wherein the diffuser extends along at least a part of an inner surface of said arm of the clip member.

21. The device of claim 20, wherein the diffuser is located between the illumination assembly and the body portion, and is formed with an optical window for allowing passage of light from the illumination assembly to the body portion.

22. The device of claim 21, wherein the diffuser is located between the body portion and the second detector unit, and is formed with an optical window allowing light passage therethrough from the body portion to the second detector unit.

23. The device of claim 21, wherein the diffuser is located between the body portion and the second detector unit, and is formed with an additional optical window allowing light passage therethrough from the body portion to the second detector unit.

24. The device of claim 19, configured for measuring in a patient's finger, said clip member enclosing the finger between its upper and lower arms.

25. The device of claim 1, comprising a clip member for enclosing the body portion between its upper and lower arms, one of the upper and lower arms carrying the illumination assembly and the second detector unit, and the other arm carrying the first detector unit, the diffuser being an elastic cover configured to wrap at least a part of the body potion under measurements, such that when the device is put in operation, the diffuser is located between the body portion and each of said arms of the clip member.

26. The device of claim 25, wherein the diffuser has at least one optical window to allow for the light passage therethrough.

27. The device of claim 25, configured for measuring in a patient's finger, said clip member enclosing the finger between its upper and lower arms.

28. The device of claim 1, configured for measuring in a patient's finger.

29. The device of claim 28, having a housing formed by two substantially U-shaped portions configured for enclosing and holding a portion of the patient's finger therebetween.

30. The device of claim 29, wherein one of the U-shaped portions carries the illumination assembly, the diffuser and the second detector unit, and the other of said portion carries the first detector unit.

31. The device of claim 29, wherein one of the U-shaped portions carries the illumination assembly and the second detector unit, and the other of said portion carries the first detector unit.

32. The device of claim 31, wherein the diffuser is an elastic cover configured to wrap at least a part of the patient's finger.

33. The device of claim 32, wherein the diffuser has at least one optical window for allowing light passage therethrough.

34. The device of claim 31, wherein the diffuser is a disposable elastic cover configured to wrap at least a part of the patient's finger.

35. The device of claim 28, comprising a pressurizing assembly associated with one of the U-shaped portions and operable for applying an over-systolic pressure to the fleshy medium so as to create a condition of artificial blood kinetics in the fleshy medium and maintain this condition for a certain time period.

36. The device of claim 35, wherein said pressurizing assembly is operable to apply a secondary controllably varying over-systolic pressure to the body portion, so as to alter said condition of artificial blood kinetics over a predetermined time interval within said certain time period, to thereby modulate scattering properties of blood.

37. The device of claim 35, wherein the pressurizing assembly comprises an air cushion extending along at least a part of an inner surface of the housing.

38. The device of claim 37, wherein at least a part of said cushion is made of a light diffusing material, thereby presenting said diffuser.

39. An optical measurement device for non-invasive measurements on a patient's finger, the device comprising:
    a ring-like housing for enclosing a portion of the finger therein;
    an illumination assembly mounted on said housing, the illumination assembly being configured and operable to direct illuminating light of a predetermined wavelength range towards a portion of the finger under measurements;
    a detection assembly mounted on said housing, the detection assembly being configured and operable to concurrently provide transmission-mode and reflection-mode of light detection, the detection assembly comprising a first transmission-mode detector unit accommodated substantially opposite the illumination assembly for detecting a first light signal indicative of the transmission of the illuminating light in the predetermined wavelength range through the finger portion in the predetermined wavelength range and generating first measured data indicative of the detected transmitted light, and a second reflection-mode detector unit operating simultaneously with said first detector and accommodated for detecting a second light signal indicative of the reflection of the illuminating light in the predetermined wavelength range from the finger portion and generating second measured data indicative of the detected reflected light;
    a light diffuser accommodated for receiving light reflected from the finger portion and re-directing the received light back towards the finger portion to thereby cause further interaction of said light with said finger portion and allowing detection of the reflected light by said second reflection-mode detection unit, thereby increasing amount of light reaching a region of interest inside the finger portion and thus maximizing homogeneity of the first and second detected light signals.

40. A method for use in non-invasive optical measurements on a patient's body utilizing illumination of a region of interest inside the body portion by illuminating light of a predetermined wavelength range and detection of light response of the region of interest, the method comprising:
    collecting at least a part of light coming from the illuminated body portion and re-directing at least a part of the collected light back to the body portion to thereby cause further interaction of said light with the body portion, light coming from the body portion including transmission of the illuminating light through the illuminated body portion and reflection of the illuminating light from the illuminated body portion;

concurrently detecting first and second light signals which are indicative of, respectively, the light transmitted through the body portion in the predetermined wavelength range and the light reflected from said body portion, and generating first measured data indicative of the detected transmitted light second measured data indicative of the detected reflected light; and analyzing the first and second measured data and generating at least one parameter related to the blood of said patient's body;

the method providing for increasing amount of light reaching the region of interest inside the body portion, and for maximizing homogeneity of the first and second detected light signals.

41. The method of claim 40, wherein said collected light coming from the body portion is light reflected therefrom.

42. The method of claim 41, wherein said collecting of the reflected light and directing at least the part thereof back to the body portion comprises locating a light diffuser in an optical path of the light reflected from the body portion.

43. The method of claim 40, wherein said collecting of the light coming from the body portion and directing at least the part of the collected light back to the body portion comprises locating a light diffuser in an optical path of the light coming from the body portion.

44. The method of claim 43, wherein the diffuser is made of a semi-transparent material, capable of diffusing visible and near-infrared light spectra.

45. The method of claim 43, wherein the diffuser is configured such that an attenuation coefficient and spatial distribution of diffused light is a very weak function of wavelength in an operating spectral rage.

46. The method of claim 43, comprising selecting a minimal size for the diffuser such as to ensure that majority of the body surface provides efficient return of reflected light to the region of interest in the body.

* * * * *